(12) United States Patent
Verdonk et al.

(10) Patent No.: US 6,306,152 B1
(45) Date of Patent: Oct. 23, 2001

(54) LANCET DEVICE WITH SKIN MOVEMENT CONTROL AND BALLISTIC PRELOAD

(75) Inventors: Edward D. Verdonk, San Jose; Paul Lum, Los Altos, both of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/264,598

(22) Filed: Mar. 8, 1999

(51) Int. Cl.$^7$ .................................................... A61B 17/34
(52) U.S. Cl. .............................................................. 606/182
(58) Field of Search ....................................... 606/181, 182, 606/183, 184; 600/573, 838, 578, 576; 604/68, 130, 134–175, 57, 64, 187–199, 239, 243, 264, 274, 272

(56) References Cited

U.S. PATENT DOCUMENTS

| | | | |
|---|---|---|---|
| 4,817,603 | * 4/1989 | Turner et al. | |
| 4,976,724 | 12/1990 | Nieto et al. | 606/182 |
| 4,983,178 | * 1/1991 | Schnell | 606/181 |
| 5,318,584 | 6/1994 | Lange et al. | 606/182 |
| 5,540,709 | * 7/1996 | Ramel | 606/182 |
| 5,554,166 | * 9/1996 | Lange et al. | 606/182 |
| 5,611,809 | 3/1997 | Marshall et al. | 606/181 |
| 5,624,458 | 4/1997 | Lipscher | 606/181 |
| 5,628,764 | 5/1997 | Schraga | 606/182 |
| 5,628,765 | 5/1997 | Morita | 606/182 |
| 5,630,828 | 5/1997 | Mawhirt | 606/187 |
| 5,643,306 | 7/1997 | Schraga | 606/182 |
| 5,645,555 | 7/1997 | Davis et al. | 606/182 |
| 5,707,384 | 1/1998 | Kim | 606/181 |
| 5,733,300 | 3/1998 | Pambianchi et al. | 606/181 |
| 5,746,761 | 5/1998 | Turchin | 606/181 |
| 5,951,493 | * 9/1999 | Douglas et al. | 606/181 |

* cited by examiner

Primary Examiner—David O. Reip

(57) ABSTRACT

A device for puncturing the skin of a patient. The device includes a lancet for puncturing the skin and a skin stabilizer associated with the lancet for stabilizing the skin to reduce its freedom of movement when the lancet strikes it. The skin stabilizer has an opening through which the lancet can pass to puncture the skin. The skin stabilizer applies pressure on the skin around the opening. The application of pressure, in additional to reducing the freedom of movement of the skin directly held by the skin stabilizer, also increases the tautness of the skin in the opening prior to the lancet penetrating the skin. The opening is not substantially larger than the size of the lancet.

20 Claims, 7 Drawing Sheets

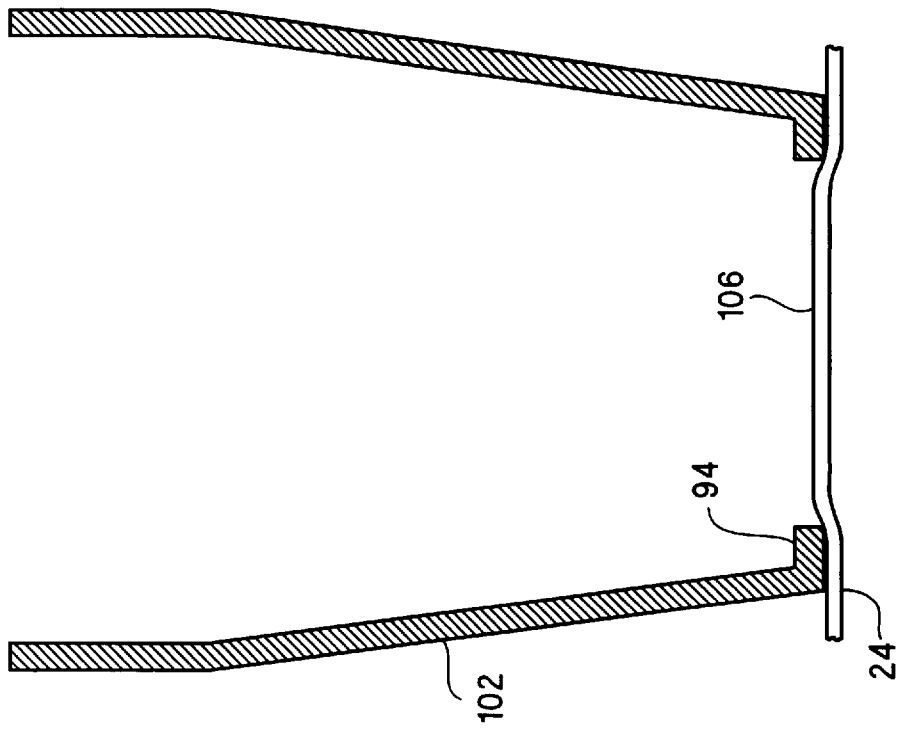
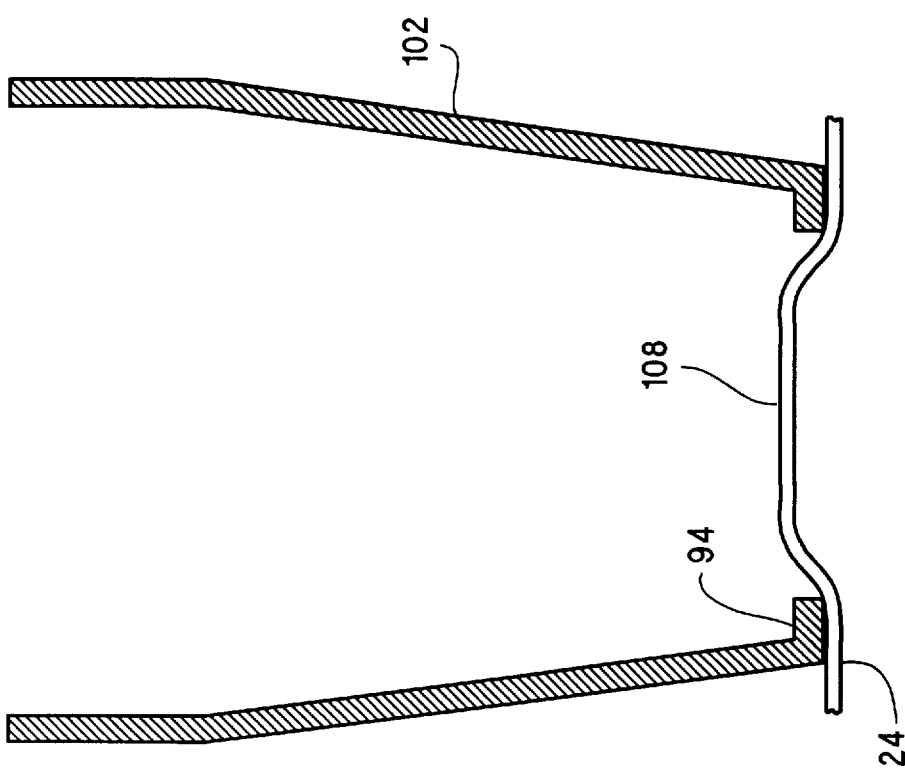

LANCET DEVICE WITH SKIN MOVEMENT CONTROL AND BALLISTIC PRELOAD

FIELD OF THE INVENTION

The present invention relates to devices for penetrating the skin to extract blood or other fluids, and more particularly, to a device for driving a lancet to puncture the skin.

BACKGROUND

Medical tests that require a small volume of blood are well known. For example, test kits for self-measurement of blood sugar levels are utilized by diabetics. These test kits require that a drop of blood be placed on a test strip that is then inserted into a measurement apparatus that displays the glucose concentration in the blood sample. To obtain the drop of blood, the user is supplied with a lancet device, which makes a skin prick, typically in the user's finger. It would be advantageous to minimize the variation between lancing episodes so that sufficient blood is obtained every time and yet the skin is not overly traumatized, since any unnecessary trauma to the skin would result in unnecessary discomfort.

To successfully obtain blood, a piercing device must traverse the skin's various layers to reach the blood vasculature. Human skin is composed of a tough, keratinized squamous epithelium. The outermost layer of skin is known as the epidermis (0.07 to 0.12 mm thick), and has its own distinct layers: stratum corneum, stratum lucidum, stratum granulosum, stratum spinosum, and stratum basale. (For a review about skin, see Tortora and Anagnostakos *"Principles of anatomy and Physiology,"* Harper and Row 1981). Underneath the epidermis is the dermis, which is 1 to 2 mm thick. Because of its varying elasticity and thickness due to the cellular structure and anatomical locations, the force necessary for penetrating the epidermis to access the vascular beds within the dermis layer will vary. It has been reported that skin tension is the greatest in the areas where the epidermal elastic keratinous fibers are dense, particularly in regions where the skin is thick, such as is found in the epigastric (stomach) regions.

To penetrate the skin surface requires a force applied normal to the surface of the skin equal to or greater than the rupture strength of the skin. Below this force level, there is first an elastic range within which the degree of deflection corresponds directly with the applied force (skin depression), followed by a non-linear response by the skin (otherwise known as the inelastic response), corresponding to the further stretching of the skin at the point of application prior to rupture. The applied force reaches a maximum when the skin ruptures, resulting in the penetration of the object into the skin. The capillary bed under the dermis is approximately 300 to 750 microns below the outer surface of the skin in the areas of the fingers, the forearms and the abdomen. Bleeding can occur when the penetration of the object reaches the capillary bed.

Many factors affect the pain sensation associated with the sampling of blood. One factor is thought to be the generation of pressure waves that are built up at the site of puncture. Providing a shallow taper to the piercing end of the lancet should reduce the pressure wave buildup, and thereby reduce the pain sensation of blood sampling.

Another successful method to minimize the pain of skin puncture by a needle, pin or lancet, is to minimize the area over which the puncture occurs. This can be achieved by miniaturizing the needle or lancet and by reducing the force applied to create the wound. The smaller the needle, the less force is required to puncture the skin, and less nerves endings are stimulated by the cut. Unfortunately, as the size of the needle used becomes smaller, the tendency of the needle to flex increases. Flexing the needle during skin penetration will increase the discomfort of the user.

Additional ways to reduce the discomfort associated with blood sampling include reducing the penetration depth of the needle into the skin and rapidly advancing and retracting the needle from the skin. Optimizing the factors to reduce patient discomfort will encourage compliance to self test, for example, for diabetic self-monitoring. Certain lancets and lancet launchers have been used. For example, U.S. Pat. No. 4,976,724 (Nieto, et al.), U.S. Pat. No. 5,318,584 (Lange, et al.); U.S. Pat. No. 5,628,764 (Schraga); U.S. Pat. No. 5,611,809 (Marshall, et al.); U.S. Pat. No. 5,624,458 (Lipscher); U.S. Pat. No. 5,628,765 (Morita); U.S. Pat. No. 5,630,828 (Marwhirt, et al.); U.S. Pat. No. 5,643,306 (Schraga); U.S. Pat. No. 5,645,555 (Davis, et al.); U.S. Pat. No. 5,707,384 (Kim); U.S. Pat. No. 5,733,300 (Pambianchi); and U.S. Pat. No. 5,746,761 (Turchin) disclose reusable or disposable launchers for lancets.

However, for blood sampling, there is still a need for a technique that can provide an adequate amount of blood with little discomfort to a patient and provide less variation in penetration depth among different lancing episodes.

SUMMARY OF THE INVENTION

The present invention provides a technique for extracting blood from the skin of a user with reduced discomfort. In one aspect, a device for puncturing the skin of a patient is provided. The device includes a lancet for puncturing the skin and a skin stabilizer associated with the lancet for stabilizing the skin peripheral to the puncture site to reduce its freedom of movement when the lancet strikes it. The skin stabilizer has an opening through which the lancet can pass. When applied to the skin, the stabilizer presses on the skin around the opening. The application of the skin stabilizer, in addition to reducing the freedom of movement of the skin under it, increases the tautness of the skin in the opening prior to the lancet penetrating the skin. The opening is not substantially larger than the size of the lancet.

The present invention can be used to advantageously lance the skin of a user with more reproducible results. Since the skin under the skin stabilizer is prevented from excessive movement and the stretching of the skin at the lancing site (in the opening not held under the skin stabilizer) is accomplished prior to the lancet contact, the variation of lancet penetration into the skin is significantly reduced between lancing episodes. With a tighter control of this variation of penetration depth, it would be much easier to reproducibly lance the skin only to the desired depth for obtaining a specific amount of blood. With better control of the penetration depth, the skin is spared the unnecessary discomfort of excessive penetration by the lancet. This will lead to better compliance of the patient self-monitoring routine prescribed by health professionals.

In an embodiment, the skin stabilizer is propelled to strike the skin to apply pressure right before the lancet is forced into the skin ballistically. The skin stabilizer provides a well-controlled and painless preload for stabilizing the skin. Furthermore, the rapid penetration of the lancet that immediately follows the preload application would result in less pain sensation, since the impact of the skin stabilizer would tend to distract the user at the time of lancet penetration. The skin stabilizer can have a bore that is mated with (i.e., closely fits) the lancet. The lancet can slide freely under guidance. Such a system will prevent lateral flexure of the lancet, thereby allowing a thinner lancet to be used.

BRIEF DESCRIPTION OF THE DRAWINGS

FIG. 2A is a schematic sectional illustration showing how skin bulges when light pressure is applied in a ring fashion on the skin.

FIG. 2B is a schematic sectional illustration showing how skin bulges when higher pressure than in FIG. 2A is applied in a ring fashion on the skin.

DETAILED DESCRIPTION OF THE INVENTION

The present invention involves a technique to reduce discomfort to a patient during lancing of the user's (or patient's) skin. The technique is based on the observation that skin may stretch, due partly to the presence of imperfections such as wrinkles or its natural elasticity, as a lancet is pressed against it, thereby requiring a lancet to move a distance before penetration. The present invention stabilizes the skin to reduce such stretching to allow better control of the penetration depth. As used herein, the term "lancet" refers to an elongated object with a sharp point for inserting into the skin to induce bleeding. Such a lancet may be needle-like with a round cross-section, or it may have cutting edge(s) along its elongated body for a cutting action to effect a less traumatic penetration into the skin. When the term "lance," "puncture," "prick" or "penetrate" is used herein regarding a lancet, unless specified otherwise, it is to be understood that any of such lancets may be used.

Figure 1B:
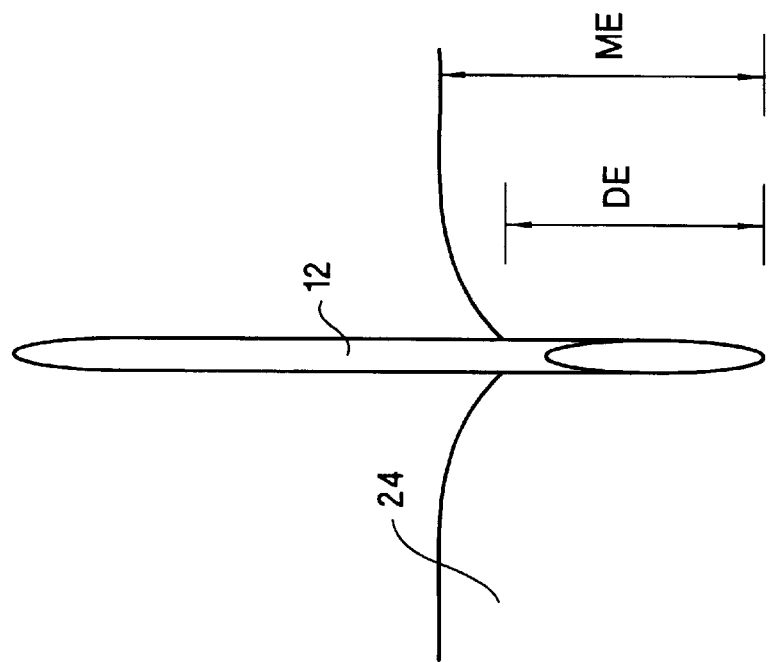
FIG. 1B is a schematic sectional illustration showing how a lancet penetrates skin that is more taut than that in FIG. 1A.
Figure 1A:
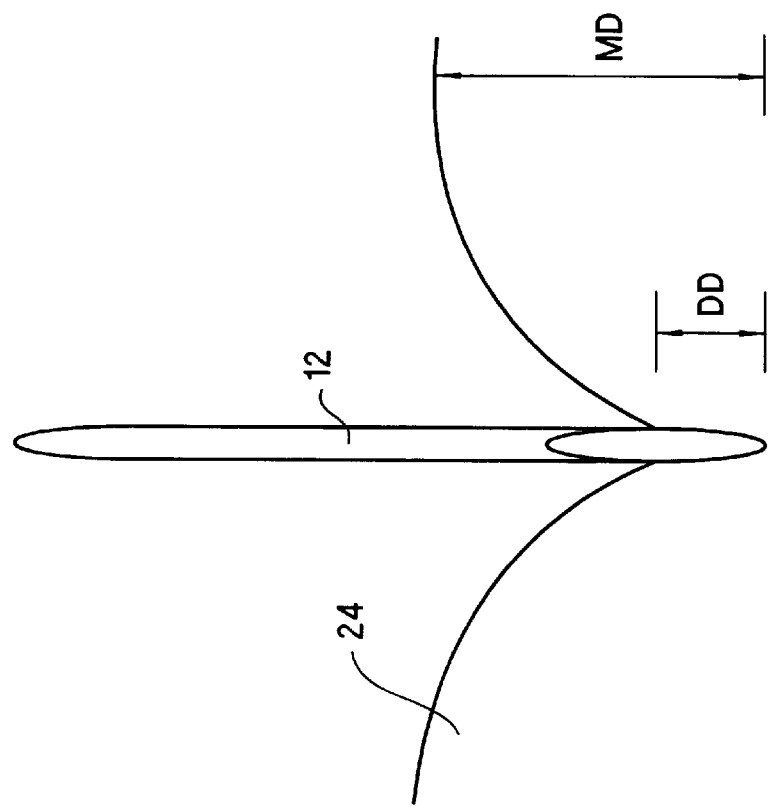
FIG. 1A is a schematic sectional illustration showing how a lancet penetrates skin that is not taut.

For any given lancet, the condition of the skin has a significant effect on the penetration of the lancet into it. For example, if the skin is wrinkled, the wrinkles tend to be smoothed out when the lancet is pushed against it. Where there are other imperfections such as scar tissues, moles, nonuniformity of tissue composition, and the like, such imperfections will also cause the amount of stretch to vary. From the time the lancet touches the skin to the time the skin is punctured, the lancet may have traveled a considerable distance. The lancet has to push the wrinkled skin until the skin is stretched taut enough to smooth out the wrinkles and exceed the puncture threshold before the lancet can penetrate. This is shown in FIG. 1A. After the lancet has begun to penetrate the skin 24, due to the lack of tautness, the depth of lancet penetration into the skin cannot be easily controlled. The arrows DD shows the depth of penetration of the lancet for the amount of lancet forward movement of arrows MD. In contrast, for skin that is taut before the lancet strikes the skin, as shown in FIG. 1B, the needle 12 penetrates the skin 24 a distance shown by arrows DE for a needle with a forward movement of a distance of ME. It can been seen that for the same distance of travel by the lancet (MD=ME), the depth of penetration is greater in the taut skin than in the less taut skin. To achieve the depth of penetration required for blood sampling, a larger distance of travel by the lancet will be needed to lance the less taut skin. Therefore, it is easier to control the depth of lancet penetration when the skin is held taut prior to lancet contacting the skin. The skin can be held taut even prior to moving the lancet forward against the skin 24.

In prior lancet technology, a lancet launcher is pressed against the skin and the lancet is launched to puncture the skin. The lancet can extend a specific distance from the end of the lancet launcher. However, because of the ability to stretch as shown in FIG. 1A and FIG. 1B, depending on how hard the lancet launcher is pressed against the skin, there can be significant variation in the depth of penetration between difference lancing episodes. The depth of penetration will be less than the extension past the end of the lancet launcher.

FIG. 2A and FIG. 2B show schematically that an end cap 102 of a lancet device is pressed (applied) against the skin 24 being lanced. Launchers including mechanisms for launching lancets to strike a finger are known in the art and will not be described in detail herein. In FIG. 2A, the end cap 102 is pressed gently against the skin 24. The lips 94 of the end cap 102 contacting the skin 24 apply a force on the skin 24 and press it slightly inward. An example of the lips 94 is an annular lip. The lips 94 can also be protrusions arranged in a ring or annular shape. The area of the skin being encircled by the annular lip, being free from any object pressing on it, will therefore extend into the central area encircled by the lips (annular lip) 94, forming a bulge 106. If the end cap 102 of the lancet device is pressed firmly against the skin 24, the skin being pressed will be under more pressure than the neighboring areas and a larger bulge 108 than the bulge 106 of FIG. 2A will result (see FIG. 2B).

Figure 3:
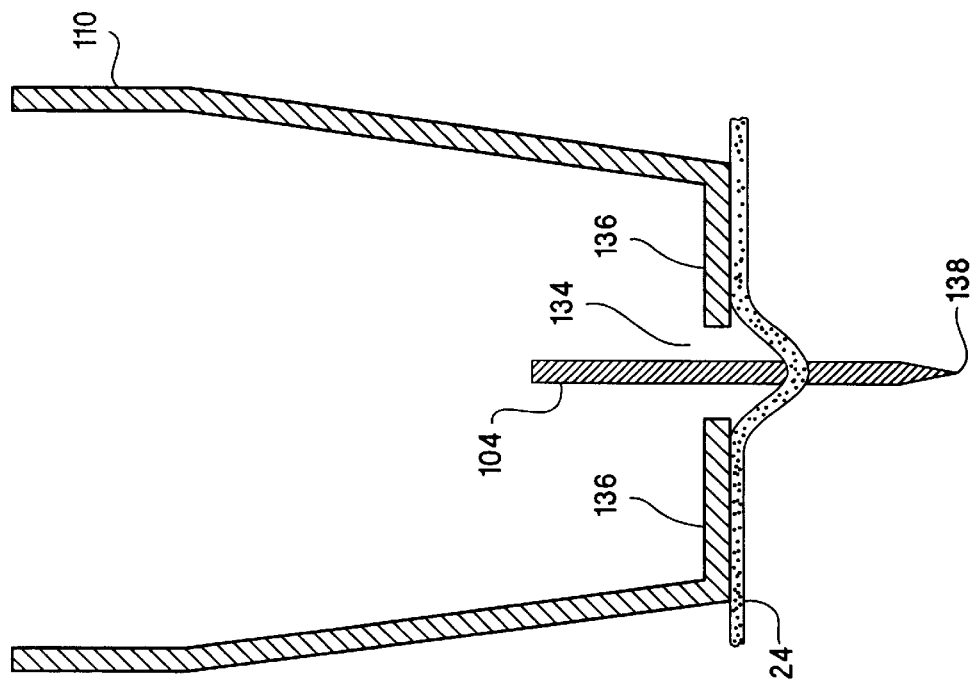
FIG. 3 is a schematic sectional view in portion of the lancet device of the present invention penetrating the skin.
Figure 9:
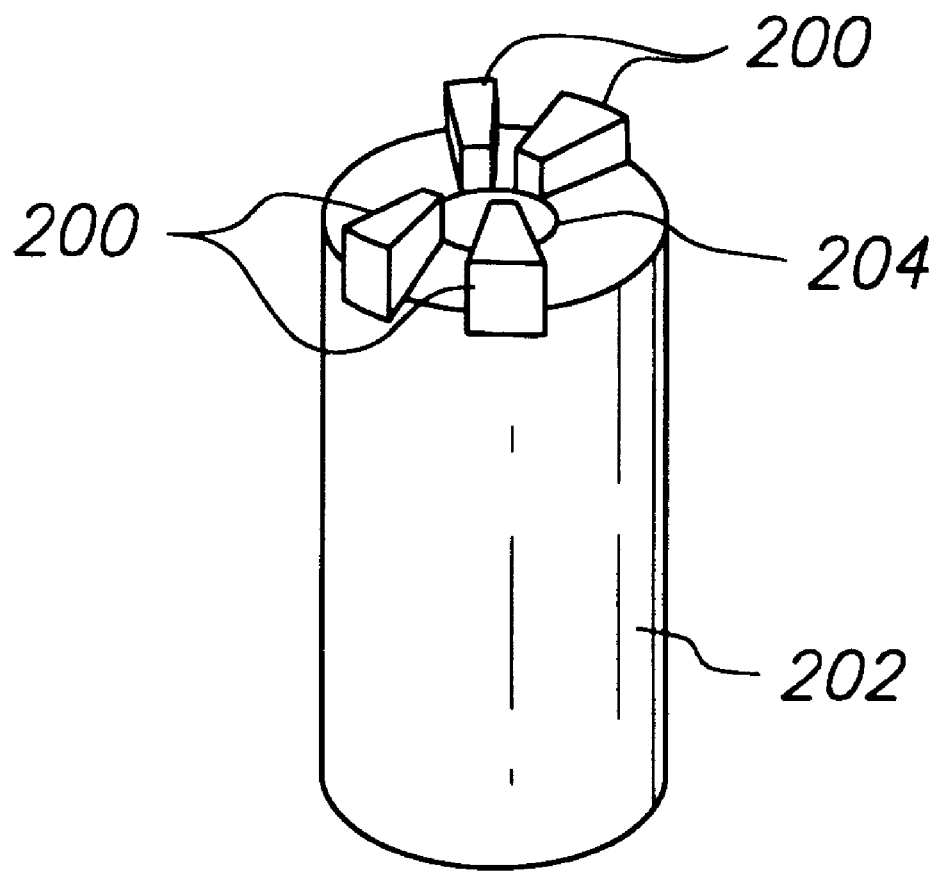
FIG. 9 is a schematic depicting an embodiment of a lancet device in accordance with the present invention wherein the device has a plurality of legs arranged in a ring-like fashion.

As previously stated, in the present invention, the lancet devices contain a skin stabilizer to stabilize the skin to minimize the skin's movement as it is penetrated by the lancet. In this way, the amount of skin that is free to stretch is minimized, thereby allowing the lancet to puncture more controllably. Further, the skin stabilizer provides a guide opening (aperture), e.g., that shown in FIG. 3, to control the lateral movement of the lancet as it passes therethrough. To illustrate the advantages of the skin stabilizer of the present invention, FIG. 3 shows schematically an end cap 110 in the lancet device. End cap 110 has an opening 134 that is about (i.e., slightly larger than) the size (i.e., the cross sectional size) of the lancet and can guide the lancet 104 as it passes through the opening during the lancing movement. The opening is the aperture at the center of lips 136 (e.g., annular lip). Preferably the aperture is not substantially larger than the size of the lancet, i.e., the aperture is about the size of the lancet to somewhat (i.e., slightly or to a small degree) larger than the lancet. Preferably the longest linear dimension of the opening is less than three time the longest linear dimension of cross section of the lancet. As used herein, the term "longest linear dimension" when used related to cross section refers to the longest straight line measurement on the cross section extending from any edge of the cross section to an opposite edge on the opposite side of the cross section. As an example, the longest linear dimension of a round cross sectional area is the diameter. For ease of manufacture, the opening as well as the cross section of the lancet preferably is round. The area of the opening 134 is preferably less than five times, more preferably less than twice the cross-sectional area of the lancet 104. Even more preferably the opening is about (i.e., only barely larger than) the size of the lancet to permit free forward lancet movement without binding. For the present invention, an example of a suitable lancet can be between about 0.1 mm to about 2 mm in diameter, depending on the amount of blood and the speed of blood emission desired in the sampling. The lips 136 held against the skin will restrict the vertical as well as the lateral movement of the skin 24 that is in contact with it. The skin held by annular lips 136 will not be able to stretch much to accommodate a lancet's forward movement without penetration. For this reason, the lips 136 applies pressures and stabilizes the skin, and can be referred as a "pressure applicator" or "skin stabilizer." Instead of using an annular lip, the skin can be stabilized with the end of a cylinder pressed on the skin. Further, the skin stabilizer can also be composed of a plurality of legs 200, arranged in a ring-like fashion on guide barrel 202 having a central bore 204 (see FIG. 9). Such a ring-like arrangement of legs, when applied to the skin, will reduce the movement and increase the tautness of the skin in the vicinity not directly in contact with the legs. The central area surrounded by the legs then becomes the opening through which the lancet can extend to lance the skin.

The opening 134, being about the size (i.e., slightly larger to allow the lancet to pass through without binding) of the lancet will limit the lateral movement of the lancet and limits its freedom to flex. Thus, even if the lancet 104, for example, when entering the skin 24, experiences a lateral force that causes it to flex, the lancet 104 will come into contact with a part of the lip 136, which will stop any further lateral movement of the lancet. The lancet 104 can slide on the lip 136 to penetrate further into the skin.

Contact of a lancet 104 with the skin 24 initiates lateral as well as vertical stretching of the skin that continues as the lancet 104 protrudes further past the end cap 110. Rapid deformation of the skin 24 results in a propagating pressure wave that stimulates nerve endings and mechanoreceptors along its path. The stressing and straining of the skin tissue continues to increase until the elastic limit of the skin has been reached. At this instant, the sharp point 138 of the lancet 104 allows the penetration of the skin tissue. For a needle-like lancet without cutting edges, upon reaching the elastic limit of the skin, tearing results due to the lack of a cutting edge. Often the shape of the wound resembled a three-pointed star. On the other hand, if a lancet has a multifaceted tip, it demonstrates the same deformation in the skin prior to penetration. However, the wound it creates is "C-shaped" due to the faceted cutting edges of the lancet.

If the amount of unclamped (i.e., exposed, not held down by the lips 136) skin surface within the opening 134 were to be reduced to approximately the diameter of the lancet, the lateral and vertical stretching of the skin upon impact of the lancet would be restricted to a more localized region, thereby allowing the elastic limit of the skin to be reached more quickly. This would result in quicker breach of the skin with the lancet tip 138 to create the required skin incision. Reducing the area of lateral and vertical stretching should result in reducing the number of nerve endings and mechanoreceptors stimulated, and hence less pain perceived by the user during lancet penetration.

Figure 4:
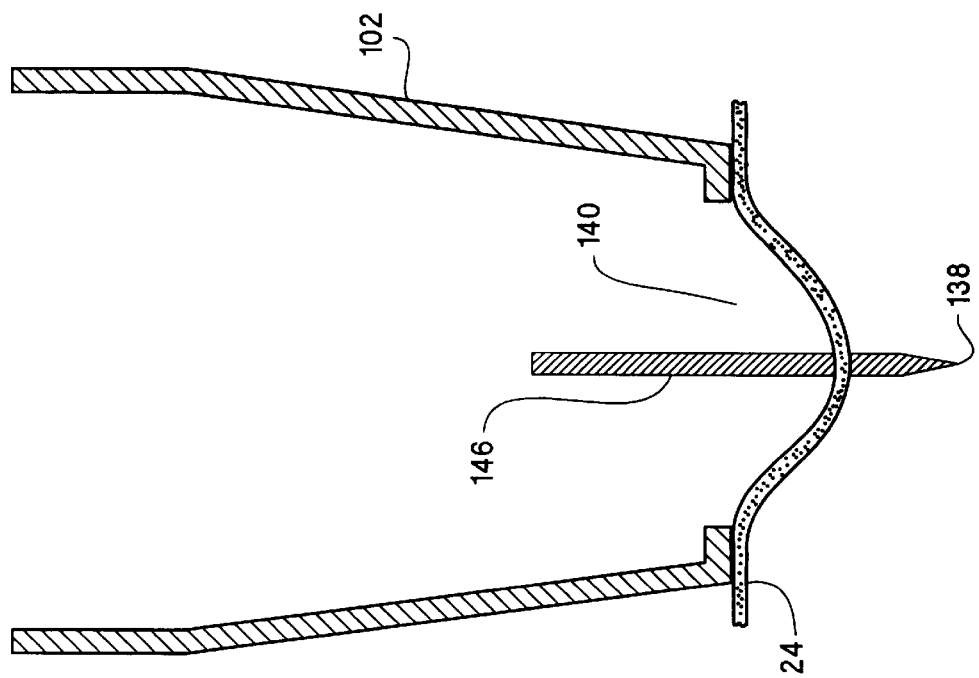
FIG. 4 is schematic sectional view in portion of the lancet device of a prior art lancet device penetrating the skin.

For comparison, the penetration depth of the lancet will be less than expected if the amount of exposed skin is large, as is done in prior technology. As shown in FIG. 4, in lancet devices of prior technology, the opening 140 through which the lancet 146 can protrude for lancing is often substantially wider than the diameter of the lancet 146. As a result, the area of skin free to stretch is substantial. For the same amount of lancet movement as that in FIG. 3, the lancet 146 in FIG. 4 will penetrate the skin to a lesser depth than in the device of present invention (see FIG. 3). Further, depending on the force with which the lancet device is held against the skin before the lancet strikes the skin (the preload), the amount of the skin bulging into the opening and the tautness of the skin can vary substantially (see FIG. 2A and FIG. 2B). Such variation can lead to significant variations of the penetration depth by the lancet, depending on how hard the lancet device is held against the skin. In contrast, with the devices of the present invention, the smaller opening permits a smaller bulge (analogous to bulge 106 in FIG. 2A), the yield strain of which is reached more rapidly than a larger bulge. The faster achievement of the yield strain will result in a more rapid and less painful lancing.

Ballistic Preload

Figure 5:
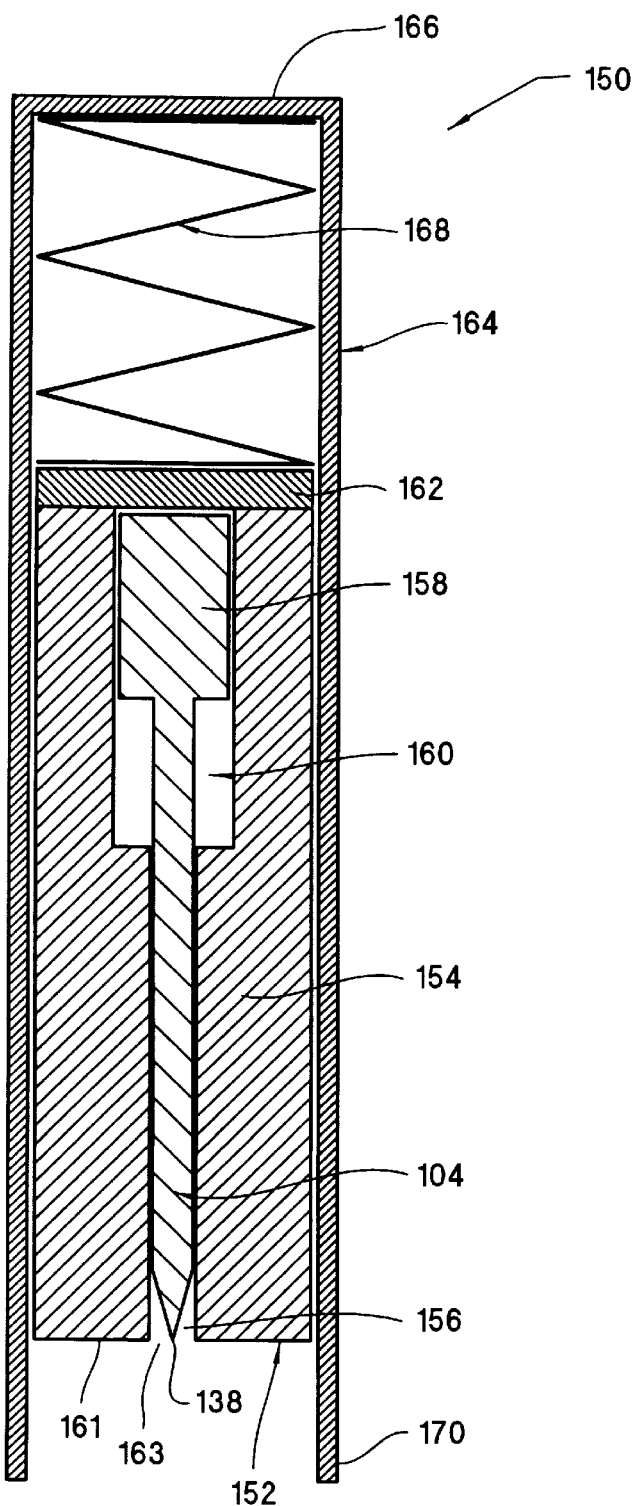
FIG. 5 shows a schematic sectional view of an embodiment of the present invention with a ballistically driven lancet and skin stabilizer.

An alternative to holding the skin stabilizer against the skin by hand (manual preload) before the lancet is launched is to use a mechanism to drive the skin stabilizer to contact the skin before the lancet is driven to lance the skin. FIG. 5 illustrates an example of a lancet device 150 that can launch a lancet and skin stabilizer. The lancet device has a skin stabilizer 152 and a lancet 104. The skin stabilizer has a guide barrel (or simply "barrel") 154 that has a central bore 156 through which the lancet can slide to protrude out of the barrel 154 for lancing. At the lancing tip of the lancet is a sharp point 138. Attached to the lancet 104 at the backward end thereof (i.e., the end opposite to the lancing sharp tip 138) is a mass (or weight or ballast) 158 such that when the lancet and the mass 158 are driven forward to lance the skin, the momentum of the lancet and the mass 158 are sufficiently large that, when the barrel 154 of skin stabilizer 152 is stopped, the momentum will carry the lancet 104 and the mass 158 forward to cause the lancet 104 to penetrate the skin to an adequate depth. The backward end of the barrel 154 has a chamber 160 in which the mass 158 attached to the lancet 104 can slide. The backward end of the chamber 160 is closed by a base plate 162, which supports the backward end of the barrel 154. The chamber 160 is longer than the mass 158 so that the mass, while attached to the lancet 104, can slide freely in the chamber 160 in both the forward and the backward directions.

The front, i.e., forward end of the barrel 154 has a surface 161, which encircles the opening 163 at the forward end of the bore 156. When the skin stabilizer 152 impacts the skin, the surface 161 presses on the skin to reduce the freedom of movement of that part of the skin.

The skin stabilizer 152 and the lancet 104 are housed in a cylindrical housing 164. A spring 168 is interposed between the cylinder's base 166 and to the base plate 162 at the backward end of the barrel 154. When the skin stabilizer 152 is pushed towards the base 166 of the housing 164, the spring 168 is compressed and stores up energy. The spring 168 may be held in the compressed state by maintaining the position of the barrel 154 relative to the cylindrical housing 164 with a triggerable catch (such as a latch, hook, clip, or similar mechanism, not shown in the figure for clarity of the illustration).

The lancet device 150 can be used by holding the device with a hand and holding the cylinder housing 164 such that its forward end 170 is against the skin. When the catch is released, i.e., when the lancet device is triggered, the spring 168 propels the skin stabilizer 152, including the lancet 104 and the mass 158 towards the skin to be lanced. When the surface 161 of the skin stabilizer 152 reaches the skin it is stopped from going further. As the skin stabilizer 152 stops, the lancet 104 and the mass 158 continue to move forward until the mass 158 encounters and is stopped by the forward end of the chamber 160. As a result, the forward end of the lancet 104 extends outside the bore 156 and penetrates the skin until the mass 158 is stopped by the chamber wall at the forward end of the chamber 160. The length of lancet 104 and the length of the bore 156 are designed such that before launching, the lancet is housed within the bore 156. When the lancet 104 is stopped by the forward end of the chamber 160, the lancet 104 will have extended out of the bore 156 and penetrated the skin to a desired depth.

Figure 6:
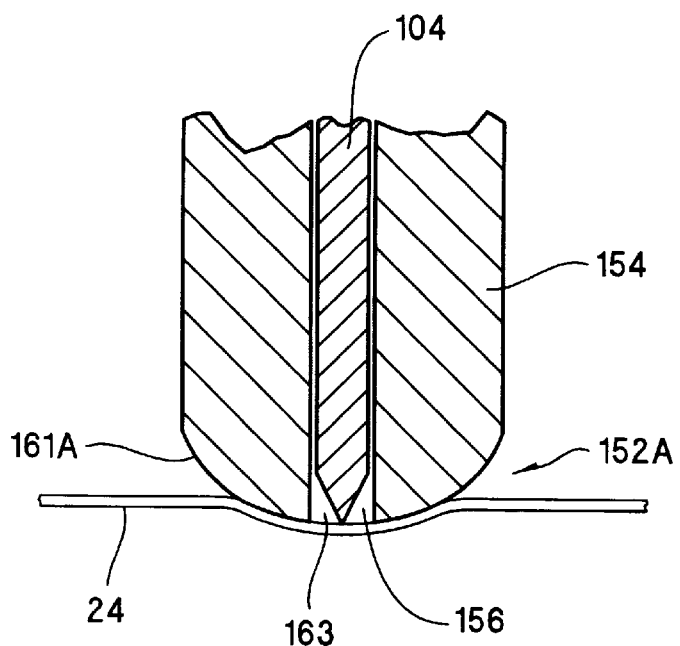
FIG. 6 shows a schematic sectional view in portion of an embodiment of a lancet device of the present invention.
Figure 7:
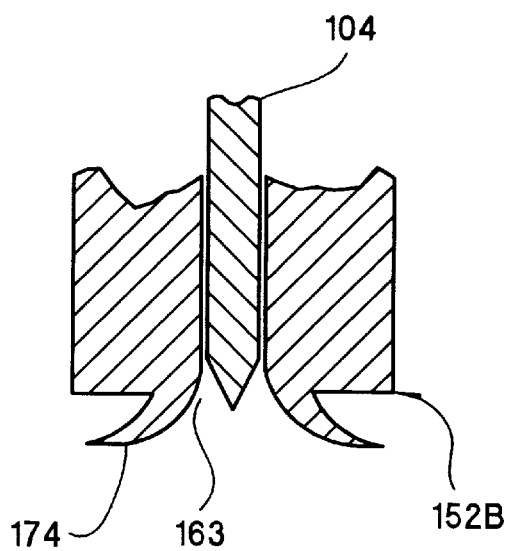
FIG. 7 shows a schematic sectional view of an embodiment of a lancet device of the present invention with a flare to contact the skin.

The spring 168 and the skin stabilizer 152 can be made such that when the skin stabilizer 152 contacts the skin the spring 168 would have fully released its stored energy such that the force exerted by the surface 161 of the skin stabilizer 152 on the skin is merely by momentum. Alternatively, the spring 168 can still be in a partially extended state such that it continues to apply active pressure to urge the surface 161 against the skin. Further, the barrel 154 can be detachable from the lancet device 150 such that both the lancet 104 and the barrel 154 can be replaced between different lancing episodes. Alternatively, only the lancet 104 and the mass 158 can be detachable so that the barrel 154 can be reused for different lancing episodes. Further, the lancet can be made to be detachable from the mass 158 so that the mass can be reused. Also, as shown in FIG. 6, the forward end of the skin stabilizer 152A can be round, except for the opening 163 to the bore 156. In this way, the surface 161A of the skin stabilizer 152A will impart the compression force on a smaller area, thereby causing a more focused application and a higher pressure where it is closer to the lancet 104 to stabilize the skin against movement. In another embodiment, as shown in FIG. 7, the forward end of the skin stabilizer 152B has a flare 174. The flare 174 is preferably made of a resiliently flexible material, such as a polymeric material with a sufficiently high coefficient of friction (e.g., silicone) such that as the flare 174 is applied to the skin, in addition to a forward component, the flare 174 directs a lateral force component on the skin to stretch it laterally (i.e., directing radially outward from the opening 163) to increase the tautness of the skin.

It is to be understood that a variety of embodiments of mechanisms to drive and withdraw the lancet can be used. For example, if the mass and the lancet are made with steel, an electrical magnet can be used to assist in the withdrawal of the lancet after the lancet has penetrated the skin. Furthermore, if desired, the mass 158 can magnetized. An electrical magnet, the magnetic property of which is controlled by electricity, can be used for propelling the magnetic mass and withdrawing it (along with the lancet attached to it). The use of magnets, including electrical magnets for propelling and withdrawing objects, are known in the art.

A further embodiment of a lancet device can include a cartridge (or a belt or ribbon) of lancets so that a lancet launcher can be coupled to the cartridge (or belt or ribbon) so that after a lancet has been used, the used lancet can be removed, and a new lancet will be properly placed for lancing. A mechanism such as that found in nail guns used for driving nails in the construction trade can be used for providing a plurality of lancets for multiple episodes of lancing.

Figure 8:
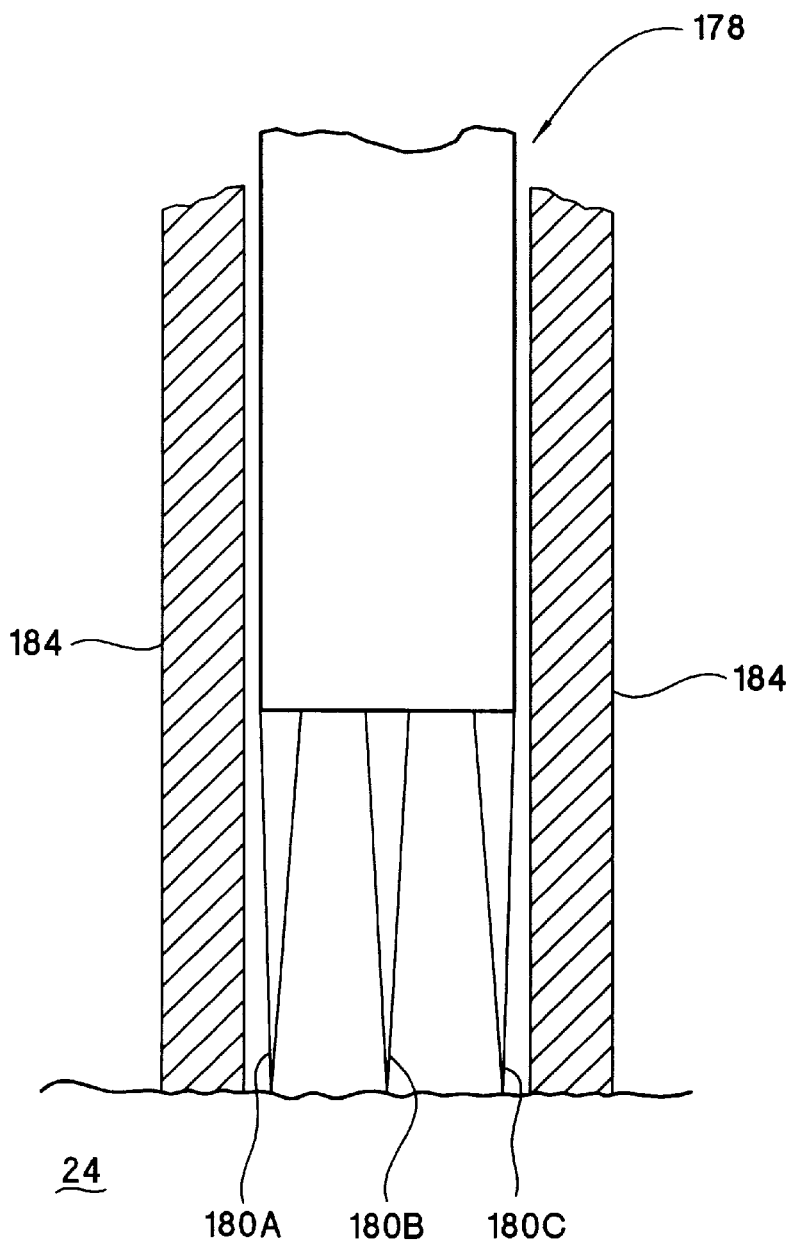
FIG. 8 shows a schematic sectional view in portion of an embodiment of a lancet device of the present invention with a multishaft lancet.

Although the above-described embodiments of the present invention have been described in terms of lancets using "needles" as a preferred embodiment, other forms of puncture devices may be utilized. For example, the puncture devices could be in the form of small oblong blades. Another example is that the lancet for penetrating the skin, instead of having a single shaft with a sharp point can be a multishaft device 178 having a number of shafts 180A, 180B, 180C (such as needles) grouped together to produce a number of puncture holes in close vicinity of one another (see FIG. 8) The stabilizer 184 increases the tautness of the skin 24. As used herein the term "lancet" can include such multishaft features. In such a case, the stabilizer 184 can be about the size of the group of shafts or somewhat larger than the group of shafts as a whole to encircle them. Copending application Attorney Docket Number 10980684-1, invented by Paul Lum et al., entitled "Multiple Lancet Device," filed on even date and commonly assigned to the same assignee as the present application, describes details of such multishaft devices, said copending application is incorporated by reference in its entirely herein. Various modifications to the present invention will become apparent to those skilled in the art from the foregoing description and accompanying drawings.

What is claimed is:

1. A device for puncturing the skin of a patient, comprising:
    (a) lancet for puncturing the skin;
    (b) skin stabilizer associated with the lancet, the skin stabilizer having an opening through which the lancet can pass to puncture the skin, the opening having a size about the size of the lancet to larger than the size of the lancet to a small degree, the skin stabilizer applying pressure around the opening to press on the skin to stabilize the skin by reducing its ability to move and increasing tautness of skin in the opening prior to the lancet penetrating the skin; and
    (c) driver mechanism to propel the skin stabilizer to contact the skin.

2. A device according to claim 1 wherein the skin stabilizer comprises a barrel having an annular forward end for applying pressure on the skin, the annular forward end provides the opening.

3. A device according to claim 2 wherein the skin stabilizer comprises a cylindrical barrel with a bore in which the lancet can slide, the barrel's forward end when applied to the skin stabilizes the skin.

4. A device according to claim 1 wherein the skin stabilizer comprises a plurality of legs, arranged in a ring-like fashion, which when applied to the skin increases the skin's tautness radially inward of the legs.

5. A device according to claim 1 wherein the skin stabilizer includes a flaring border lip surrounding the opening such that when the border lip is pressed against the skin the border lip exerts force on the skin with a component of the force directing radially outward from the opening.

6. A device according to claim 1 wherein the opening has a longest linear dimension and the lancet has a longest linear dimension of cross section and wherein the longest linear dimension of the opening is larger than the size of the lancet by less than three times the longest linear dimension of cross section of the lancet.

7. A device according to claim 1 wherein the lancet has a cross section and a cross-sectional area and the opening has an area and wherein the cross section of the lancet is disk-shaped and the area of the opening is larger than the size of the lancet by less than 5 times the cross-sectional area of the lancet.

8. A device according to claim 1 wherein said mechanism is a driver for driving the skin stabilizer and the lancet, and wherein the lancet is slidably connected to the skin stabilizer such that when they are driven together toward the skin, if the skin stabilizer is stopped by the skin, the lancet will continue its forward motion for a sufficient distance with sufficient force to penetrate the skin to cause bleeding.

9. A device according to claim 8 further comprising a spring which can be retained in a compressed form for release to propel the skin stabilizer and the lancet toward the skin for lancing.

10. A device according to claim 8 wherein the driver comprises a spring for propelling the skin stabilizer and the lancet and wherein the lancet is rigidly connected to a mass sufficiently heavy that when the skin stabilizer is stopped by the skin after propulsion the lancet and the mass will have sufficient momentum to penetrate the skin to a sufficient depth to cause bleeding.

11. A device according to claim 1 further comprising a means anchored to the stabilizer for preventing the skin stabilizer from sliding off the skin when the skin stabilizer is applied to the skin.

12. A method of using a lancet device to puncture the skin of a patient, comprising:
(a) using a driver mechanism to mechanically propel a skin stabilizer to stabilize the skin to reduce its freedom of movement by putting pressure on the skin at one or more locations surrounding a central area not in contact with the stabilizer when the stabilizer is applied to the skin; and
(b) puncturing the skin with a lancet at the central area thereafter, wherein the central area which is not in contact with the skin stabilizer is not substantially larger than the cross-sectional size of the lancet.

13. A method according to claim 12 further comprising applying a cylindrical skin stabilizer to press on the skin in an annular form around the lancet to stabilize the skin.

14. A method according to claim 12 further comprising applying pressure on a plurality of points arranged in a ring-shape around the lancet to stabilize the skin.

15. A method according to claim 12 further comprising applying to the skin a force having a lateral component directing radially outward to increase the tautness of the skin before the lancet penetrates the skin.

16. A method according to claim 12 further comprising mechanically propelling the skin stabilizer and the lancet toward the skin and wherein the skin stabilizer is stoppable by the skin without penetration whereas the lancet will continue to move forward after the skin stabilizer has been stopped.

17. A method according to claim 12 comprising using sufficient mass to provide sufficient momentum to the lancet such that the lancet will penetrate the skin by momentum to a sufficient depth to cause the skin to bleed.

18. A method of using a puncturing device to puncture an object with a stretchable surface layer, comprising:
(a) using a driver mechanism to mechanically propel a stabilizer to contact and stabilize one or more areas of the surface layer to reduce its freedom of movement, the one or more areas encircling a central area not in contact with the stabilizer; and
(b) puncturing the surface layer at the central area with a shaft having a sharp end thereafter, wherein the central area which is not in contact with the stabilizer is not substantially larger than the cross-sectional size of the shaft.

19. A method according to claim 18 further comprising mechanically propelling a stabilizer and the shaft toward the surface layer, wherein the stabilizer is stoppable by the surface layer without penetration, whereas the shaft will continue to move toward the object by momentum to penetrate the surface layer to a predetermined depth before stopping.

20. A device for puncturing the skin of a patient, said device comprising:
(a) lancet for puncturing the skin, the lancet having a mass associated therewith;
(b) skin stabilizer associated with the lancet, the skin stabilizer having an opening through which the lancet can pass to puncture the skin, the skin stabilizer, when applied on the skins, applying pressure around the opening to press on the skin to increase tautness thereof prior to the lancet penetrating the skin, the lancet being movably connected to the skin stabilizer, the skin stabilizer being stoppable by the skin without penetration when driven toward the skin by a driver, the lancet having sufficient mass to continue by momentum to move forward to penetrate the skin sufficiently to cause bleeding after the skin stabilizer has stopped; and
(c) spring-actuated driver associated with the skin stabilizer and the lancet for propelling the skin stabilizer and the lancet toward the skin.

* * * * *